United States Patent [19]

Gaudreault et al.

[11] Patent Number: 5,530,026

[45] Date of Patent: Jun. 25, 1996

[54] CERTAIN ARYL-UREIDO ANTI-CANCER AGENTS

[75] Inventors: René C. Gaudreault, Bernières; Patrick Poyet, Saint-Rédempteur, both of Canada

[73] Assignee: Universite Laval, Quebec, Canada

[21] Appl. No.: 369,584

[22] Filed: Jan. 6, 1995

Related U.S. Application Data

[63] Continuation of Ser. No. 25,848, Mar. 3, 1993, abandoned.

[51] Int. Cl.$^6$ .................. A61K 31/275; C07C 229/48; C07C 275/26; C07C 275/28

[52] U.S. Cl. .................. 514/524; 514/534; 514/596; 514/597; 514/598; 560/19; 560/20; 560/34; 558/418; 564/48; 564/49; 564/50; 564/52; 564/53

[58] Field of Search .................. 564/48, 49, 50, 564/52, 53; 558/418; 560/19, 20, 34; 514/524, 534, 596, 597, 598

[56] References Cited

U.S. PATENT DOCUMENTS

| | | | |
|---|---|---|---|
| 3,968,249 | 7/1976 | Bernstein et al. | 514/588 |
| 4,150,154 | 4/1979 | Diamond et al. | 514/596 |
| 4,202,890 | 5/1980 | Gale et al. | 514/110 |
| 4,291,062 | 9/1981 | Leigh et al. | 514/588 |
| 4,304,786 | 12/1981 | Diamond et al. | 514/211 |
| 4,623,662 | 11/1986 | De Vries | 514/596 |
| 4,707,478 | 11/1987 | Studt et al. | 514/580 |
| 4,803,223 | 2/1989 | Kato | 514/521 |
| 4,898,886 | 2/1990 | Amat-Larraz | 514/588 |
| 4,973,675 | 11/1990 | Israel et al. | 536/6.4 |

OTHER PUBLICATIONS

J. Pharmaceutical Sciences, 1988, 77(2), 185–187.
Anticancer Research, 1988, 8, 595–598 (Lacroix et al.).
J. Med. Chem., 1966, 9, 892–911 (Johnston et al.).
J. Med. Chem., 1963, 6, 669–681 (Johnston et al.).

Primary Examiner—Alan L. Rotman
Attorney, Agent, or Firm—Merchant & Gould, Smith, Edell, Welter & Schmidt

[57] ABSTRACT

The present invention is concerned with novel anticancer agents having potent antineoplastic activity without systemic toxicity and mutagenicity. The novel anticancer agents of the present invention are derivatives of formula I:

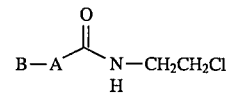

wherein:

A is O or NH; and

B is an aryl group selected from the group consisting of phenyl, indane, fluorene, indazole, indole, and pyridine, the aryl group being substituted with at least one substituent selected from the group consisting of hydrogen, $C_{1-16}$ alkyl optionally substituted with one or more OH or SH, lower alkoxy, $C_{3-6}$ cycloalkyl, lower alkylthio, nitro, cyano, lower alkene, lower alkyne, OH, SH, carboxy lower alkyl, carboxy lower alkyl esters, amino, N-lower alkyl, N,N-dilower alkyl and halogen;

or a prodrug thereof, with the provisos that when A is NH and B is phenyl:

a) B is substituted with at least one substituent other than hydrogen;

b) B is not:

1) mono-substituted in the 4 position with $C_{1-2}$ alkyl, tert-butyl or n-butyl, halogen, OH, carboxy $C_{0-3}$ alkyl, $(CH_2)_3COOCH_3$, cyano, acetyl and methylthio; and 2) substituted with one or two identical substituents selected from the group consisting of methyl, halogen, nitro, methoxy, carboxy and $C_{0-3}$ alkyl COOH, the remaining substituents being hydrogen atoms.

10 Claims, No Drawings

CERTAIN ARYL-UREIDO ANTI-CANCER AGENTS

This is a continuation application Ser. No. 08/025,848, filed Mar. 3, 1993, now abandoned.

BACKGROUND OF THE INVENTION

Chemotherapeutic agents currently used for antitumor therapy are selected for their toxicity towards rapidly proliferating cells. Most of them cause undesirable systemic effects such as cardiac or renal toxicity, marrow aplasia, alopecia, nausea and vomiting. During the last few years, many authors have tried to eliminate these side effects by developing drugs having suitable physico-chemical properties allowing an increase of the availability of the drug to the tumors site. New molecules extracted from natural sources, synthetically or semi-synthetically produced, enzymes, radioisotopes, DNA toxins, various macromolecules, and antibodies against fibrin or against tumor-specific surface antigens are bound to drugs in an attempt to increase selectivity of the chemotherapeutic agents.

It is recognized that the ideal antineoplastic or anticancer drug would destroy cancer cells without adverse effects or toxicities on normal cells, but such drug has yet to be discovered. However, despite the narrow therapeutic index of many drugs, treatment and even cure are possible in some patients.

Chlorambucil and carmustine are commonly used antineoplastic agents from respectively the class of nitrogen mustards and nitrosoureas. They can be administered orally or intravenously, but these drugs cause nausea, vomiting, alopecia, lymphopenia, leucopenia and bone marrow depression. Their biological half-life is short (approximately 1–1.5 h) with a high percentage bound to plasma proteins (over 90%). Both nitrogen mustard and nitrosourea derivatives are extensively metabolized, yielding active and inactive metabolites.

Nitrogen mustard and nitrosourea derivatives are particularly effective in treating Hodgkin's disease and non-Hodgkin's lymphomas. In fact, they are among the most active synthetic molecules ever synthesized. Indeed, chlorambucil is used at doses up to 6 mg/m$^2$ and carmustine is active in primary brain tumors because it crosses easily the blood brain barrier at low doses.

In *J. Med. Chem.*, 1966, 9, 892–910, Johnston et al. discloses several N-nitrosoureas as potential anti-cancer agents. Corresponding urea derivatives were mainly used as intermediates for the synthesis of the nitrosoureas. Among the urea derivatives tested in vitro, non of them showed activity. Other examples of antitumor agents of the same family are disclosed in Clinical and Invest. Med, 1985, 49 (Gaudreault et al.); *J. Pharm. Science*; 1988, 77, 185 (Gaudreault et al.); *Anticancer Research*, 1988) 8, 595 (Gaudreault et al.); and *J. Med Chem*, 1963, 6, 669 (Johnston et al).

The effectiveness of most anticancer agents is greatly reduced because of their high toxicity and the nature of the illness. It is believed that the problem of high toxicity of the anticancer agents can be circumvented by chemical modifications of those structures in such a way that they act more specifically on tumor cells without increasing systemic toxicity.

The research in this field is therefore mainly directed to the synthesis of anticancer agents which would possess high antineoplastic activity, low systemic toxicity and low mutagenicity on normal cells. Preferably, such anticancer agents would possess an extended shelf life without experiencing polymerization or decomposition problems, and could be handled by anyone having minimal knowledge of this subject. Finally, such anticancer agents would be prepared easily in large quantities.

SUMMARY OF THE INVENTION

In accordance with the present invention, there is now provided novel anticancer agents which have potent antineoplastic activity without systemic toxicity and mutagenicity. The novel anticancer agents of the present invention are compounds of formula I:

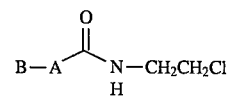

wherein:

A is O or NH; and

B is an aryl group selected from the group consisting of phenyl indane, fluorene, indazole, indole, and pyridine, the aryl group being substituted with at least one substituent selected from the group consisting of hydrogen, $C_{1-16}$ alkyl optionally substituted with one or more OH or SH, lower alkoxy, $C_{3-6}$ cycloalkyl, lower alkylthio, nitro, cyano, lower alkene, lower alkyne, OH, SH, carboxy lower alkyl, carboxy lower alkyl esters, amino, N-lower alkyl, N,N-dilower alkyl and halogen;

or a prodrug thereof, with the provisos that when A is NH and B is phenyl:

a) B is substituted with at least one substituent other than hydrogen;

b) B is not:

1) mono-substituted in the 4 position with $C_{1-2}$ alkyl, tert-butyl or n-butyl, halogen, OH, carboxy, $C_{0-3}$ alkyl, $(CH_2)_3COOCH_3$, cyano, acetyl and methylthio; and 2) substituted with one or two identical substituents selected from the group consisting of methyl, halogen, nitro, methoxy, carboxy and $C_{0-3}$ alkyl COOH, and the remaining substituents being hydrogen atoms.

These compounds are useful in treating cancer tumors, and show a significant increase of pharmacological activity and a major decrease of toxicity when compared to known nitrogen mustard and nitrosourea currently in use. The compounds of the present invention are also highly stable at room temperature, do not decompose and are conveniently and easily prepared at low costs by a simple process.

DETAILED DESCRIPTION OF THE INVENTION

The compounds of the present invention are easily synthesized in good yields without polymerization or decomposition. They are also easily purified by usual crystallization or liquid chromatography. Furthermore, they are not decomposed in the presence of air, at room temperature, which means that their shelf life is extended.

The type and level of activity for a given dosage of each compound can be conventionally determined by routine experimentation using well known pharmacological protocols for each of the activities. The corresponding indications treatable at that dosage will be readily appreciated by skilled workers based on the pharmacological results.

As an example of prodrug for the compounds of the present invention, there may be mentioned the sulfone and sulfoxide derivatives of alkylthio substituents. The sulfone and sulfoxide derivatives are generally not active as such, but once administered, they are reduced to yield the corresponding alkylthio, which is active as an anticancer agent.

Preparation of compounds of formula I

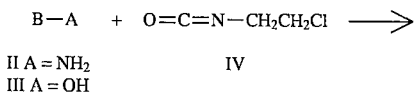

II A = NH$_2$
III A = OH
IV

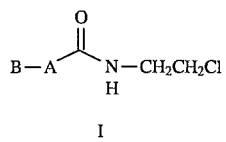

I

If A is NH, an amine derivative of formula II wherein B is as defined above is reacted with an isocyanate of formula IV in anhydrous ether under nitrogen atmosphere at room temperature for 2 to 16 hours or until the disappearance on thin layer chromatography (TLC) of the starting amine of formula II. The solid residue obtained is filtered and dried in vacuo, the filtrate is evaporated under reduced pressure, and the solid remaining therein is also dried in vacuo. Both solids are independently recrystallized with suitable organic solvents and the final crystals are pooled after evaluation of their purity by chromatography, IR, $^1$H NMR and MS. Where the crystallization is difficult, a purification by column chromatography on silica gel may be required prior to the final crystallization. The compounds of formula I wherein A is NH are finally dehydrated in vacuo for several hours.

If A is O, the compounds of formula I are obtain by reacting an alcohol of formula III with isocyanate IV in pyridine for about 3 hours at room temperature. It should be noted that pyridine can be replaced with ether containing 15 mmoles of triethylamine. The solvent is evaporated and the residue is washed with cold ethanol or ether before being recrystallised in ethanol containing 0.1% of acetic acid to lead to the desired product.

Following the procedures of the present invention, the following compounds of formula I wherein A is NH have been prepared:

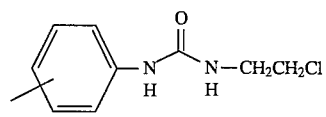

| Product Number | Nature and Positions of Substitutions | | | | |
|---|---|---|---|---|---|
| | 2 | 3 | 4 | 5 | 6 |
| 1 | | | (CH$_2$)$_3$CH$_2$OH | | |
| 2 | | ethyl | | | |
| 3 | | | propyl | | |
| 4 | | | isopropyl | | |
| 5 | | | sec-butyl | | |
| 6 | | | n-pentyl | | |
| 7 | | | n-hexyl | | |
| 8 | | | cyclohexyl | | |
| 9 | | | n-heptyl | | |
| 10 | | | n-octyl | | |
| 11 | | | n-decyl | | |
| 12 | | | n-dodecyl | | |
| 13 | | | n-hexadecyl | | |
| 14 | | ethoxy | | | |
| 15 | | | pentoxy | | |
| 16 | | | hexyloxy | | |
| 17 | methyl | | methyl | | methyl |
| 18 | ethyl | | | | |
| 19 | ethyl | | ethyl | | |
| 20 | propyl | | | | |
| 21 | isopropyl | | | | isopropyl |
| 22 | isopropyl | | | | methyl |
| 23 | tert-butyl | | | tert-butyl | |
| 24 | methoxy | | | methyl | |
| 25 | methoxy | | | | methyl |
| 26 | methyl | | | methoxy | |
| 27 | methyl | | methoxy | | |
| 28 | ethoxy | | | | |
| 29 | | | ethoxy | | |
| 30 | | | butoxy | | |
| 31 | | | Cl(CH$_2$)$_2$NHC(O)NH | | |
| 32 | OH | | | | |
| 33 | | OH | | | |
| 34 | CN | | | | |
| 35 | | | (CH$_2$)$_2$CH$_2$OH | | |
| 36 | | | CH$_2$CH$_2$OH | | |
| 37 | | | (CH$_2$)$_3$CH$_2$OOCCH$_3$ | | |
| 38 | | | (CH$_2$)$_2$CH$_2$OOCCH$_3$ | | |
| 39 | | | SCH$_2$CH$_3$ | | |

The following compounds of formula I wherein A is O have been prepared.

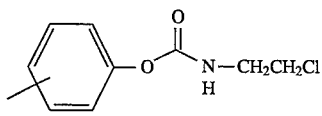

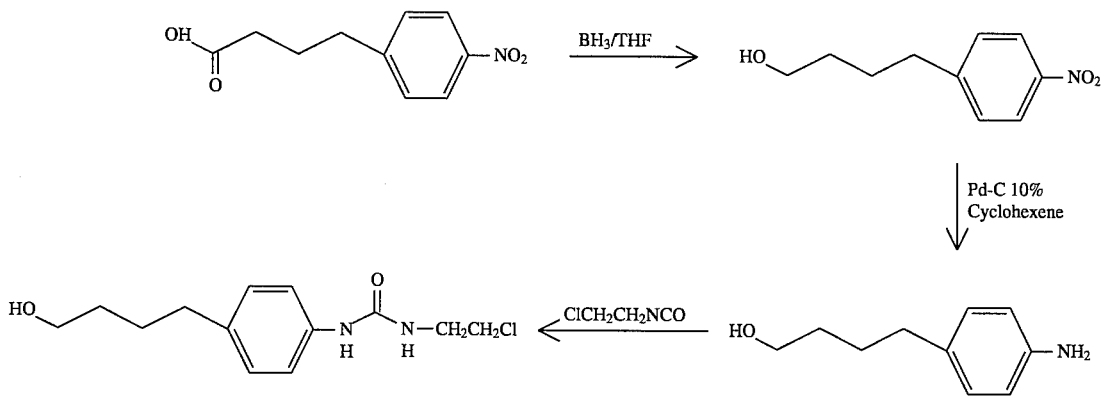

| Product Number | Nature and Positions of Substitutions | | | | |
|---|---|---|---|---|---|
| | 2 | 3 | 4 | 5 | 6 |
| 40 | | | nitro | | |
| 41 | | methoxy | | | |
| 42 | methoxy | | | | |
| 43 | | | methoxy | | |
| 44 | methoxy | | | | methoxy |
| 45 | methoxy | methoxy | | | |
| 46 | | methyl | | | |
| 47 | | methyl | nitro | | |
| 48 | | | methyl | | |
| 49 | methyl | | | | |
| 50 | | methyl | methyl | | |
| 51 | methyl | | | methyl | |
| 52 | methyl | methyl | | methyl | |
| 53 | | | tert-butyl | | |
| 54 | tert-butyl | | | | |
| 55 | allyl | | | | |
| 56 | | | isopropyl | | |
| 57 | | isopropyl | | | |
| 58 | isopropyl | | | | |
| 59 | | | butaxy | | |
| 60 | | | acetamido | | |
| 61 | | acetamido | | | |
| 62 | | | Cl | | |
| 63 | | Cl | | | |
| 64 | Cl | | | | |
| 65 | | | F | | |
| 66 | | F | | | |
| 67 | F | | | | |

The experimental evidence provided below indicates that the pharmacological activity of the compounds of the present invention are significantly more cytotoxic than the nitrogen mustard chlorambucil used as standard. The derivatives tested are stable at room temperature for several months without any detectable decomposition or decrease of cytotoxic activity. The procedure of preparation is simple, reproducible and most reagents are commercially available.

The present invention will be more readily understood by referring to the following examples which are given to illustrate the invention rather than to limits its scope.

EXAMPLE I

Preparation of 4-{p-[3-(2-chloroethyl)ureido]phenyl}butanol

(p-Nitrophenyl) butyric Acid 4-phenylbutyric acid (1; 20 g) is dissolved in 140 mL of concentrated nitric acid. The resulting solution is stirred at room temperature for 6 h and subsequently poured onto 500 g of crushed ice to yield a yellow solid. The 4-nitrophenyl isomer 2 is recrystallized from isopropyl alcohol at 4° C. (yield 22%, mp 92°–93° C.). Upon further cooling of the etheral solution (–20° C.), the 4-nitrophenyl isomer 3 separated as pale yellow crystals (yield 50%, mp 58°–59° C.).

4-(p-nitrophenyl) butanol

Borane:THF complex ($BH_3$:THF, 33.3 mmoles) is slowly added over a period of 15 minutes to a cooled solution (0° C., ice bath) of 4-(p-nitrophenyl) butanol (2.5 mmoles) dissolved in 12.5 mL of anhydrous THF. The solution is then further stirred for 2 hours at room temperature. The excess of $BH_3$:THF complex is destroyed with the addition of 10 mL of water, and the resulting solution is subsequently saturated with potassium carbonate, the organic phase is separated, and the aqueous portion extracted with with 3×30 mL of ether. The organic solutions are pooled, washed with 3×30 mL of sodium carbonate 2N, dried over anhydrous magnesium sulfate, and evaporated under reduced pressure to provide a yellow oily residue: yield 90%; IR: 3350 (OH), 1560, 1360 ($NO_2$) $cm^{-1}$; $^1H$ NMR ($CDCl_3$): 8.3–7.3 (dd, 4p, ArH p-substituted), 3.65 (t, 2p, $ArCH_2$), 2.82 (t, 2p, $CH_2OH$), 2.24 (s, 1p, $CH_2OH$), 1.85 (q, 2p, $ArCH_2CH_2$), 1.45 (q, 2p, $CH_2CH_2OH$).

4-(p-aminophenyl)butanol

A mixture of ethanol 99% and cyclohexene (3:1 v/v) containing 4-(p-nitrophenyl) butanol (2.5 mmoles) and 10% Pd/C (5 mmolar equivalent) is refluxed for 16–18 h, filtered over silica gel column (5×15 cm$^2$) to remove the palladium on carbon. The column is washed with 50 ethanol 99% and the organic solution is evaporated under reduced pressure to provide a yellow oily product (yield 95%), readily used for the preparation of 4-{p-[3-(2-chloroethyl)ureido]phenyl} butanol without any further purification.

4-{p-[3-(2-chloroethyl)ureido]phenyl}butanol

To a solution of 4-(p-amino phenyl) butanol (2 g in 125 mL of ethyl ether) is added dropwise 1.25 g of 2-chloroethyl isocyanate. This solution is stirred for 3 h at room temperature, cooled at −20° C., and faltered. A white solid of 4-{p-[3-(2-chloroethyl)ureido]phenyl} butanol is separated and recrystallized from ethanol (white flakes), yield 55%, mp 123°–124° C., IR (KBr pellet): 3300 (NH), 1730 (C=O, ester), and 1640 cm$^{-1}$(C=O, ureido); $^1$H NMR (DMSO-d$_6$): 8.65 (s, 1p, ArNH), 7.4-7.0 (dd, 4p, p-substituted Ar), 6.4 (broad t, 1p, NHCH$_2$), 3.7-3.4 (m, 6p, ArCH$_2$ and NHCH$_2$CH$_2$Cl), 2.85 (t, 2p, CH$_2$OH), 2.3 (s, 1p, CH$_2$OH), 1.85 (q, 2p, CH$_2$CH$_2$CH$_2$), 1.45 (q, 2p, CH$_2$CH$_2$OH)

EXAMPLE II

Preparation of sec-butyl-4-{p-[3-(2-chloroethyl)ureido} benzene

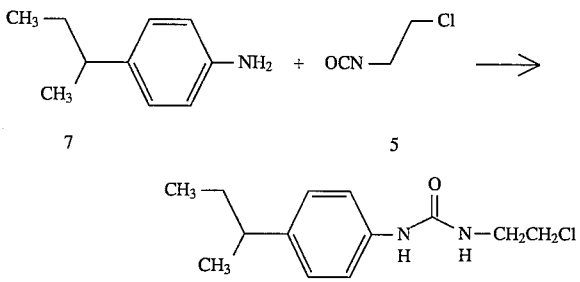

To a solution of 2 g of sec-butyl aniline, 7 in 125 mL of anhydrous ethyl ether is added dropwise, 1.25 g of 2-chloroethyl isocyanate, 5. This solution is stirred for 6 h at room temperature, cooled at −20° C., and faltered. A brownish solid separated and was recrystallized from ethanol. Yield 80%, mp 89°–91° C., IR (KBr pellet): 3300 (NH), 1730 (C=O, ester), and 1640 cm$^{-1}$ (C=O, ureido); $^1$H NMR (DMSO-d$_6$: CDCl$_3$): 7.791 ppm (s, 1p, ArNH); 7.232 ppm, 7.190 ppm, 7.016 ppm, 6.974 ppm (m, 4p, ArH); 6.053 ppm (t, 1p, CONH); 3.578 ppm, 3.562 ppm, 3.540 ppm, 3.516 ppm, 3.496 ppm, 3.472 ppm (m, 4p, CH$_2$CH$_2$Cl); 2.516 ppm, 2.481 ppm, 2.446 ppm, 2.411 ppm (m, 1p, CH$_3$-CH); 1.557 ppm, 1.520 ppm, 1.483 ppm, 1.447 ppm, 1.411 ppm (m, 2p, CH$_3$-CH-CH$_2$-CH$_3$), 1.145 ppm, 1.110 ppm (d, 3p, CH$_3$-CH-CH$_2$CH$_3$); 0.772 ppm, 0.737 ppm, 0.699 ppm (t, 3p, CH3-CH-CH$_2$-CH$_3$).

EXAMPLE III

Preparation of 4-[p-[3-(2-chloroethyl)ureido] phenyl ethanol

This compound was prepared according to the process of Example 2, except that 4-(p-amino phenyl)ethanol was used. Yield 65%, M.P. 127°–128° C., IR (KBr pellet) 3300 (OH), 1660 (C=O ureido) cm$^{-1}$, $^1$H NMR (CDCl$_3$) 8.5 (s, 1p, ArNH), 7.6-7.2 (dd, A$_2$B$_2$ system for p-substituted ArH), 6.4 (broad t, 1p, NHCH$_2$), 3.9-3.6 (m, 6p, ArCH$_2$ and CH$_2$CH$_2$Cl), 3.0 (t, 2p, CH$_2$OH), 2.75 (s, 1p, CH$_2$OH).

EXAMPLE IV

Preparation of isopropyl-4-{p-[3-(2-chloroethyl)ureido} benzene

This compound was prepared according to the process of Example 2, except that isopropyl aniline was used instead of sec-butyl aniline. Yield 65%, R (KBr pellet) 3400, 3310; 1650; 1220, 680 cm$^{-1}$, $^1$H NMR (CDCl$_3$) 7.87 ppm, 7.15-7.00, 6.05 ppm, 3.45 ppm, 2.7 ppm, 1.11-1.07 ppm.

EXAMPLE V

Preparation of 2-[3-(2-chloroethyl)ureido] fluorene

To a solution of 2 g of 2-aminofluorene in 125 mL of anhydrous ethyl ether is added dropwise 1.25 g of 2-chloroethyl isocyanate. This solution is stirred for 16 h at room temperature, cooled at −20° C., and filtered. A white solid separated and was recrystallized from ethanol (white flakes), yield 40%, mp 206°–208° C., IR (KBr pellet): 3300 (NH), 1730 (C=O, ester), and 1640 cm$^{-1}$ (C=O, ureido); $^1$H NMR (DMSO-d$_6$: CDCl$_3$): 8.08 ppm, 7.44 ppm, 7.35 ppm, 7.3 ppm, 7.27 ppm, 7.25 ppm, 7.16 ppm, 7.13 ppm, 7.02 ppm, 6.97 ppm, 6.96 ppm, 6.94 ppm, 6.93 ppm, 6.9 ppm, 6.87 ppm, 6.8 ppm, 3.5 ppm, 3.36 ppm, 3.33 ppm, 3.3 ppm, 3.25 ppm, 3.23 ppm, 3.2 ppm, 2.85 ppm.

EXAMPLE VI

Preparation of 5-[3-(2-chloroethyl)ureido] indane

To a solution of 2 g of 5-aminoindane in 125 mL of anhydrous ethyl ether was added dropwise, 1.25 g of 2-chloroethyl isocyanate. This solution is stirred for 16 h at room temperature, cooled at −20° C., and filtered. A white solid separated and was recrystallized from ethanol (white flakes), yield 40%, mp 155°–157° C., IR (KBr pellet): 3300 (NH), 1730 (C=O, ester), and 1640 cm$^{-1}$ (C=O, ureido); $^1$H NMR (DMSO-d$_6$: CDCl$_3$): 6.96 ppm, 3.52 ppm, 3.49 ppm, 3.46 ppm, 3.43 ppm, 2.74 ppm, 2.72 ppm, 1.93 ppm. In this spectrum hydrogen present on NH groups have exchanged with the presence of DMSO-d$_6$.

EXAMPLE VII

Preparation of 6-[3-(2-chloroethyl)ureido] indazole

To a solution of 2 g of 6-aminoindazole in 125 mL of anhydrous ethanol is added, in a dropwise manner, 1.25 g of 2-chloroethyl isocyanate. This solution is stirred for 16 h at room temperature, cooled at °20° C., and filtered. A white solid separated and was recrystallized from ethanol, yield 30%, mp 253°–258° C. $^1$H NMR (DMSO-d$_6$: CDCl$_3$): 8.12 ppm, 7.56 ppm, 7.44 ppm, 7.25 ppm, 7.12 ppm, 7.08 ppm, 6.43 ppm, 6.39 ppm, 6.01 ppm, 5.98 ppm, 5.96 ppm, 3.42 ppm, 3.4 ppm, 3.39 ppm, 3.54 ppm, 3.26 pm, 3.23 ppm, 3.2 ppm, 3.17 ppm, 3.14 ppm, 3.12 ppm, 3.09 ppm, 3.05 ppm, 3.04 ppm, 3.04 ppm.

EXAMPLE VIII

Preparation of 5- [3-(2-chloroethyl)ureido] 4,6-dimethyl pyridine

To a solution of 2 g of 2-amino 4, 6-dimethyl pyridine in 125 mL of anhydrous ethyl acetate is added dropwise 1.25 g of 2-chloroethyl isocyanate. This solution was stirred for 16 h at room temperature, cooled at −20° C., and filtered. A white solid separated and was recrystallized from methanol and the final product washed with ether (white powder), yield 67%, mp 122°–124° C. $^1$H NMR (DMSO-d$_6$: CDCl$_3$): 9.93 ppm, 6.42 ppm, 3.65 ppm, 3.63 ppm, 3.6 ppm, 3.59 ppm, 3.51 ppm, 2.27 ppm, 2.11 ppm.

EXAMPLE IX

Preparation of 5-[3-(2-chloroethyl)ureido] indole

To a solution of 2 g of 5-aminoindole in 125 mL of anhydrous acetone is added dropwise 1.25 g of 2-chloroethyl isocyanate. This solution was stirred for 16 h at room temperature, cooled at °20° C., and filtered. The solvent is evaporated and the residue was crystallized from methanol and washed with ether to give a brownish solid, yield 30%, mp 159°–161° C.

EXAMPLE X

Preparation of 4-nitro phenyl N-(2-chloroethyl) carbamate 12 mmoles of 2-chloroethyl isocyanate were slowly added to 10 mmoles of 4-nitrophenol dissolved in 40 ml of anhydrous pyridine and maintained at 20° C. The mixture was stirred at 20° C. for 3 hours. The solution was evaporated in vacuo and the residue washed several times with cold ethanol and cold ether. The residue was dried in vacuo and recrystallized from ethanol 95% containing 0.1% of acetic acid. Yield 80%, melting point 92°–93° C., $^1$H NMR (CDCl$_3$) 8.0-7.16 ppm (dd, A$_2$B$_2$, 4p, ArH substituted in 1,4 positions); 5.44 (singlet, 1p, NHCH$_2$); 3.64 (singlet, 4p, NHCH$_2$CH$_2$Cl). Pyridine can be replaced with a mixture of anhydrous ether containing 15 mmoles of triethylamine, in order to avoid the use of noxious and toxic pyridine.

Cell Lines

Cells lines are used to show that the compounds of the present invention are potent cytotoxic agents and active on various normal and tumor cell lines. As suitable cell lines there may be mentioned: human adenocarcinoma cells (CRL-229, LoVo), human ovarian carcinoma cells (CRL-1572), human breast cancer cells (MDA-MB-231), normal mouse breast cells (HC-11), mouse leukaemia cells (CCL-46, P388D$_1$), mouse leukaemia (CCL-219, L1210), CRL-1427, human promonocyte U937 and the like. Most of these cell lines are readily available from the American Type Culture Collection. Cells lines: O-23, O-23 clone 2.2, LR-73, LR-73 MDR-3, T47D and T47D (GST), having developed resistance to antineoplastic agents through different mechanisms of resistance were also tested in the same manner.

All cell lines are cultured by a standard procedure in RPMI-1640® medium supplemented with 10% fetal bovine serum and 100 μg/mL of penicillin and 100 μg/mL of streptomycin.

In vitro cytotoxicity

In order to evaluate the efficiency of the compounds of formula I, the following experiments are carried out. Cytotoxicity assays are conducted on LoVo, MDA-MB-231 and P388D$_1$ cells. The choice of these cells has been motivated by the fact that they have been specifically identified as the cause of a large number of cancer in North America in the recent years.

Tumor cells are obtained from the American Type Culture Collection. The cells are suspended at a concentration of 2.5×10$^4$ cells/mL in a fresh culture media (RPMI-1640, supplemented with 10% fetal calf serum). The well plates (microtitration, 96 wells) are seeded with 100 μL of the cell suspension and incubated 24 hours at 37° C. in a humid atmosphere containing 5% CO$_2$. 100 μL of fresh culture media containing different concentrations of drugs to be tested (1 to 25 μM) are added in 8 wells of each plate, and the cells are further incubated for 3 additional days at 37° C. under the same conditions. Each experiment is conducted in triplicate. Cell survival is determined by MTT method, as taught in *J. Immunol. Methods*, 1986, 89, 271 (Denizot et al.) and *Int. J. Immunopharm.*, 1988, 10, 785 (Page et al). The method mainly consisted of a rest removal of the culture media and addition to the plates of 20 μL of a MTT solution (5 mg/mL in PBS pH 7.4). The plates are incubated at 37° C. for 4 hours and then 200 μL of dimethylsulfoxide (DMSO) area added into the wells. The plates are agitated for 15 rain at room temperature and the absorbance at 540 nm measured on Titertek MC Multiwell® spectrophotometer.

The method normally used by the American National Cancer Institute for the comparison of effectiveness between drugs is based upon ID$_{50}$. The ID$_{50}$ is the concentration at which half of tumor cell population is killed. A comparison of the antitumor agents of the present invention with chlorambucil, which is presently used commercially, is provided to illustrate the superiority of the former. The results are shown in Tables 1 and 2.

TABLE 1

ID$_{50}$ of products deriving from examples V, VI, VII, VII, IX on various cancer cell lines

| Example No. | ID$_{50}$(μM) on tumor cells | | |
|---|---|---|---|
| | LoVo | MDA-MB-231 | P388D$_1$ |
| V | 5 | 4 | 4 |
| VI | 5 | 7 | 7 |
| VII | 31 | 29 | 76 |
| VIII | — | 50 | — |
| IX | — | 70 | — |

TABLE 2

| Compound | ID$_{50}$ (μM) (MDA-MB-231) | ID$_{50}$ (μM) (LoVo) | ID$_{50}$ (μM) (P388 D$_1$) |
|---|---|---|---|
| 2 | 7.8 | 3.5 | 7 |
| 3 | 12 | 9.8 | 11 |
| 4 | 2 | 1.3 | 2.2 |
| 5 | 2.2 | 1.6 | 2.4 |
| 6 | 6 | 5.5 | 7.0 |
| 7 | 73 | 6.2 | 7.9 |
| 8 | 29 | 22 | 22 |
| 9 | 16 | 15 | 18 |
| 10 | 33 | 29 | 32 |
| 14 | 33 | 35 | 42 |
| 15 | 22 | 16 | 28 |
| 16 | 22 | 16 | 17 |
| 39 | 17 | — | — |
| 40 | 10 | 7 | 82 |
| 47 | 7.5 | 72 | 8 |
| 50 | 40 | 30 | 40 |
| 63 | 8.5 | 7.5 | 5 |
| Chlorambucil | 11 | 9 | 6.7 |

Though the inventors have chosen a given method for evaluating the in vitro cytotoxicity of the compounds of the present invention, it will be obvious to those skilled in the art that any other conventional method can be used for that purpose.

Mutagenicity assay.

The mutagenicity assay was performed with the Ames test as taught in *Mutation Research*, 1983, 113, 173–215. Briefly, 500 μL of the drug to be tested are dissolved in DMSO, 500 μL of S9 mix (obtained from rat liver stimulated with arochlor) or phosphate buffer and 100 μL of either TA-97, TA-98, TA-100 or TA-102 *S. thyphimurium* strains ($1\times10^8$ bacteria) were mixed with 2 ml of top agar. The medium was poured onto the dish containing 30 ml of minimal glucose agar. Chlorambucil, CCNU, compound 5 was tested in duplicate at 50, 125, 250, 375 and 500 μg/dish. Dishes were incubated for two days at 37° C. and revertant colonies counted with a Biotran III counter.

Toxicity assay

Chlorambucil and compound 36 of the present invention were dissolved in DMSO. Each drug solution was mixed with hydrogenated soybean oil in a ratio 1:9 v/v. 100 μL of this mixture was administered i.p. to $BDF_1$ (C57BL/6× DBA/2) mice. For each concentration of drug varying from 9.25 to 75 mg/kg for chlorambucil or from 9.25 to 296 mg/kg for compound 36, 6 mice were treated. Survival weight and fitness were measured as criteria of toxicity. The results are provided in Table 3.

TABLE 3

STUDY ON THE ACUTE TOXICITY OF UREA DERIVATIVES OF THE INVENTION ON SWISS MICE

| product number | 9.25 mg/kg | 18.5 mg/kg | 37 mg/kg | 75 mg/kg | 111 mg/kg | 148 mg/kg | 222 mg/kg | 296 mg/kg |
|---|---|---|---|---|---|---|---|---|
| chlorambucil | 6/6 | 6/6 | 6/6 | 0/6 | — | — | — | — |
| 36 | 6/6 | 6/6 | 6/6 | 6/6 | 6/6 | 6/6 | 6/6 | 6/6 |

Antineoplastic assay

L1210 leukaemia cells suspended in RPM1-1640 were washed, centrifuged and re-suspended in phosphate buffer saline (PBS) at a concentration of $5\times10^5$ cells/mL. 200 μL of the suspension were injected i.p. to $BDF_1$ mice. From day 1 to day 9, mice were treated daily according to the NCl procedure taught in Protocols for screening chemical agents and natural products against animal tumors and other biological systems ($3^{rd}$ edition). Cancer Chem. Rep. Part 3 3 (2): 1–103) with i.p. injections of 10 μL of drug solution in DMSO mixed with 90 μL of hydrogenated soybean oil. Chlorambucil was tested at 1, 5 and 10 mg/kg/day and compounds 36 and 4 at 1, 10 and 50 mg/kg/day. For each concentration, six mice were treated. Control groups were treated i.p. with 100 μL of hydrogenated soybean oil containing 10% (v/v) DMSO.

The antineoplastic activity of a drug on mice bearing cancer tumors is evaluated by a value known in the art as the median survival time (T/C %). This value of T/C % is obtained by dividing the median survival time of treated mice by that of untreated mice, and the quotient is multiplied by 100. When the value of T/C % is lower than 85, the drug is considered toxic. On the other hand, a survival time greater than 125 indicates a significant antineoplastic action of the drug on cancer tumors. In the above experiment, chlorambucil, compounds 36 and 4 had a T/C % of 160, 140 and 164 respectively, at 10 mg/kg.

While the invention has been described in connection with specific embodiments thereof, it will be understood that it is capable of further modifications and this application is intended to cover any variation, uses, adaptations of the invention following, in general, the principles of the invention and including such departures from the present disclosure as come within known and customary practice within the art to which the invention pertains and as may be applied to the essential features hereinbefore set forth, and as follows in the scope of the appended claims.

What is claimed is:

1. A compound of the formula I:

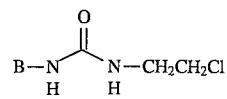

wherein:

B is an aryl group selected from the group consisting of indanyl, substituted indanyl, fluorenyl and substituted fluorenyl;

wherein the substituted indanyl and substituted fluorenyl have substituent selected from the group consisting of $C_1$–$C_{16}$ alkyl, $C_1$–$C_{16}$ hydroxyalkyl, $C_1$–$C_{16}$ mercaptoalkyl, lower alkoxy, $C_3$–$C_6$ cycloalkyl, lower alkylthio, nitro, cyano, lower alkene, lower alkyne, hydroxyl, mercapto, carboxy lower alkyl, amino, N-loweralkyl, N,N-diloweralkyl and halogen.

2. A pharmaceutical composition for treating adenocarcinoma, breast cancer or leukemia comprising a compound according to claim 1 in association with a pharmaceutically acceptable carrier.

3. A compound according to claim 1, consisting of a prodrug wherein the aryl group is substituted with a mercapto alkyl sulfonyl group or an alkyl sulfoxyl group.

4. A method for treating patients with adenocarcinoma, breast cancer or leukaemia which comprises administering to the patient a therapeutically effective amount of a compound according to claim 1.

5. A compound according to claim 1, of the formula 2-[3-(2-chloroethyl)ureido] fluorene.

6. A compound according to claim 1, of the formula 5-[3-(2-chloroethyl)ureido] indane.

7. A compound according to claim 1, of the formula 2-[ 3-(2-chloroethyl )ureido] fluorene.

8. A compound according to claim 1, of the formula 5-[3-(2-chloroethyl)ureido]indane.

9. A compound of the formula II:

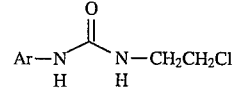

wherein:

Ar is a phenyl group having one, two or three meta or para branched $C_3$–$C_8$ alkyl groups.

10. A compound according to claim 3, which is selected from the group consisting of: 4-sec butyl-1- [3- (2-chloroethyl) ureido] benzene; 2, 5-di tert butyl-1- [3 - (2 -chloroethyl) ureido] benzene.

* * * * *

UNITED STATES PATENT AND TRADEMARK OFFICE
CERTIFICATE OF CORRECTION

PATENT NO. : 5,530,026

DATED : June 25, 1996

INVENTOR(S) : Gaudreault et al.

It is certified that error appears in the above-identified patent and that said Letters Patent is hereby corrected as shown below:

Col. 5, line 53 delete "methyl" (in col. 5 of table), insert --methyl-- (in col. 6 of table)

Col. 8, line 51, "°20°C." should read -- -20°C. --

Col. 9, line 13, "°20°C." should read -- -20°C. --

Col. 10, line 12 "rest" should read --first--

Col. 10, line 17 "rain" should read --min--

Col. 10, line 51 "73" should read --7.3--

Col. 10, line 58 "82" should read --8.2--

Col. 10, line 59 "72" should read --7.2--

Col. 12, line 24 insert --a-- after the word "have"

Signed and Sealed this

Third Day of December, 1996

Attest:

BRUCE LEHMAN

Attesting Officer     Commissioner of Patents and Trademarks